(12) United States Patent
Aizenberg et al.

(10) Patent No.: US 7,883,665 B2
(45) Date of Patent: Feb. 8, 2011

(54) CHEMICAL AND BIOLOGICAL DETECTION ARRAYS

(75) Inventors: Joanna Aizenberg, New Providence, NJ (US); Thomas Nikita Krupenkin, Warren, NJ (US); Oleksandr Sydorenko, Bryn Mawr, PA (US); Joseph Ashley Taylor, Springfield, NJ (US)

(73) Assignee: Alcatel-Lucent USA Inc., Murray Hill, NJ (US)

( * ) Notice: Subject to any disclaimer, the term of this patent is extended or adjusted under 35 U.S.C. 154(b) by 1236 days.

(21) Appl. No.: 11/226,576

(22) Filed: Sep. 14, 2005

(65) Prior Publication Data

US 2007/0059488 A1 Mar. 15, 2007

(51) Int. Cl.
G01N 21/00 (2006.01)
G01N 15/06 (2006.01)
G01N 33/53 (2006.01)
B32B 9/04 (2006.01)

(52) U.S. Cl. .................. 422/58; 428/447; 422/68.1; 435/7.1

(58) Field of Classification Search .............. 422/58, 422/68.1; 428/447; 435/7.1
See application file for complete search history.

(56) References Cited

U.S. PATENT DOCUMENTS

| 4,233,029 A * | 11/1980 | Columbus ................. 436/174 |
| 5,124,172 A * | 6/1992 | Burrell et al. .................. 435/4 |
| 6,720,157 B2 * | 4/2004 | Indermuhle et al. .......... 435/7.1 |
| 7,223,364 B1 * | 5/2007 | Johnston et al. ............ 422/68.1 |
| 2003/0175534 A1 * | 9/2003 | Chen et al. ................. 428/447 |
| 2005/0026346 A1 * | 2/2005 | Blankenstein et al. ....... 438/200 |
| 2005/0042766 A1 | 2/2005 | Ohman et al. ............... 436/174 |
| 2007/0047388 A1 * | 3/2007 | DeNatale et al. ............ 366/341 |

FOREIGN PATENT DOCUMENTS

WO WO 01/62887 A1 8/2001
WO WO 03/022421 A2 3/2003

OTHER PUBLICATIONS

U.S. Appl. No. 10/999,249, filed Nov. 30, 2004 entitled Reversibly Adaptive Rough Micro- and Nano-Structures (36 pgs).

* cited by examiner

Primary Examiner—Lore Jarrett
(74) Attorney, Agent, or Firm—Jay M. Brown

(57) ABSTRACT

Device comprising: a first substrate; a plurality of first raised elements on the first substrate, the first raised elements mutually spaced apart by first channel regions on the first substrate, each of the first raised elements having a first distal end, the first distal ends forming a first array; hydrophobic molecules on the first raised elements; and primary reactive molecules on the first raised elements for generating hydrophilic reaction products. Techniques for utilizing the device.

20 Claims, 8 Drawing Sheets

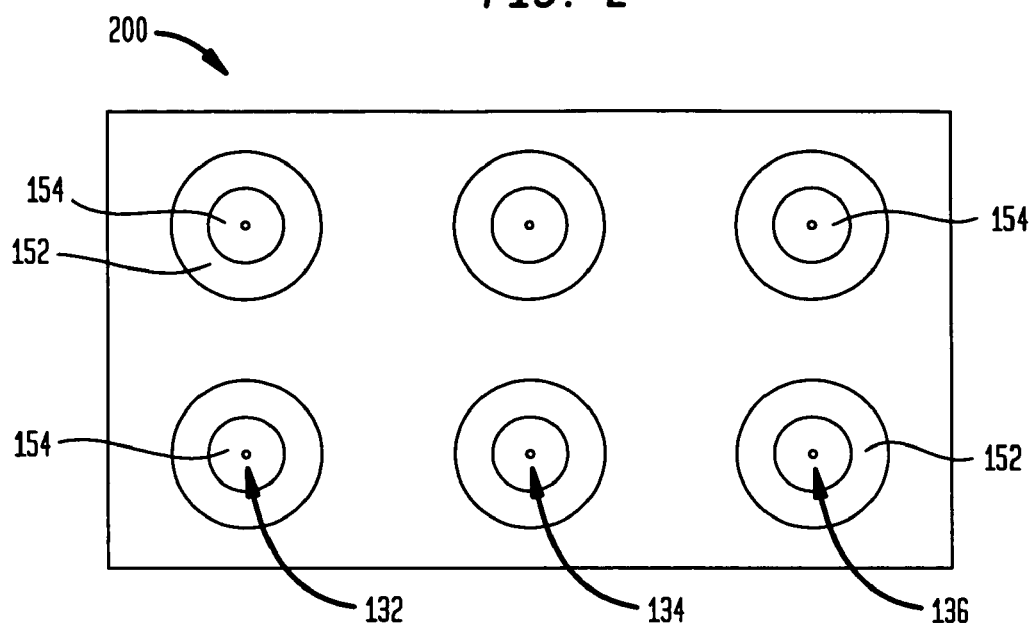
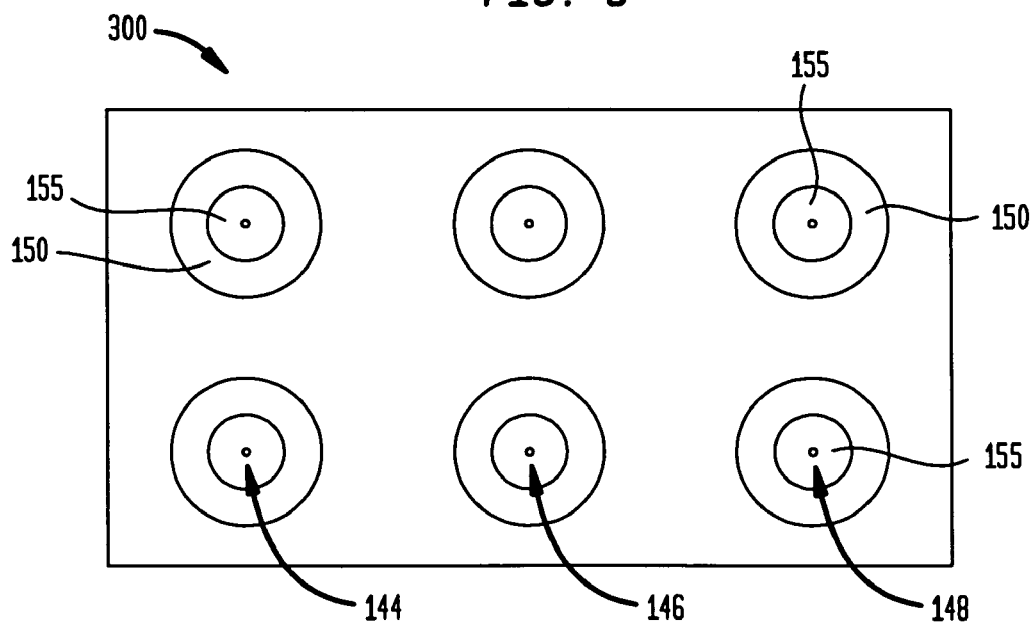

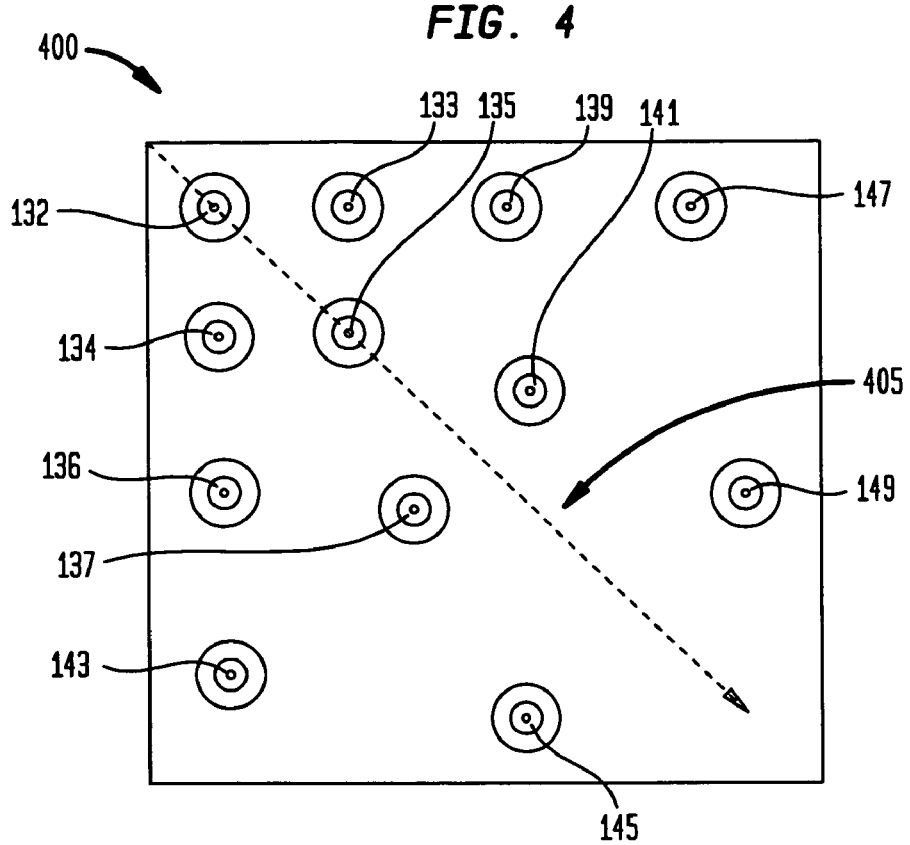
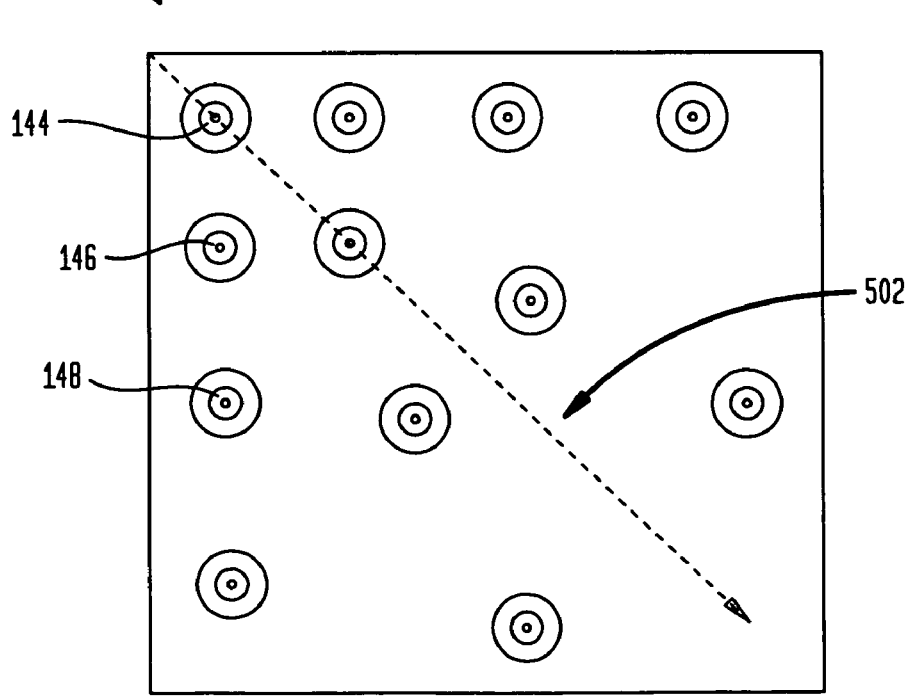

CHEMICAL AND BIOLOGICAL DETECTION ARRAYS

FIELD OF THE INVENTION

The present invention relates to the field of chemical and biological detection arrays.

BACKGROUND OF THE INVENTION

Many types of detectors for materials of unknown chemical or biological composition have been developed. For example, arrays of biological and chemical probes having a variety of specific binding properties have been made, often referred to as biochips or labs-on-a-chip. Myriad other devices are available for identification of unknown molecules, such as organic pollutants.

There is a continuing need for devices that may be used to direct samples of an unknown material into a large number of different potential interactions with known materials so that detected interactions between the known and unknown materials may be employed to identify the unknown materials.

SUMMARY OF THE INVENTION

In one example of an implementation, a device is provided, comprising: a first substrate; a plurality of first raised elements on the first substrate, the first raised elements mutually spaced apart by first channel regions on the first substrate, each of the first raised elements having a first distal end, the first distal ends forming a first array; hydrophobic molecules on the first raised elements; and primary reactive molecules on the first raised elements for generating hydrophilic reaction products.

In another implementation, a method is provided, comprising the step of: providing a device having: a first substrate; a plurality of first raised elements on the first substrate, the first raised elements mutually spaced apart by first channel regions on the first substrate, each of the first raised elements having a first distal end, the first distal ends forming a first array; hydrophobic molecules on the first raised elements; and primary reactive molecules on the first raised elements for generating hydrophilic reaction products. The method further comprises the steps of: bringing a hydrophilic liquid into contact with first raised elements; and determining whether a hydrophobicity-changing reaction occurs between primary reactive molecules on first raised elements and the hydrophilic liquid.

BRIEF DESCRIPTION OF THE DRAWINGS

FIG. 2 shows first distal ends which are included within a portion of a first array;

FIG. 3 shows second distal ends which are included within a portion of a second array FIG. 4 shows a first array portion;

FIG. 5 shows a second array portion;

DETAILED DESCRIPTION

Devices are provided that include a plurality of raised elements on a substrate. Distal ends of the raised elements constitute an array, over which a hydrophilic liquid may be moved. Hydrophobic molecules are placed on the raised elements. Reactive molecules are also placed on the raised elements. Reactions between the hydrophilic liquid and reactive molecules on raised elements may cause a region of the array to become less hydrophobic or to become hydrophilic. A portion of the hydrophilic liquid localized in such a region of the array may then be caused to descend, between raised elements, downward to channel regions on the substrate. The localized presence of the liquid within channel regions on the substrate may then be detected. Further reactive molecules may be placed within channel regions. Reactions between the liquid and reactive molecules within channel regions may then also be detected. A plurality of different reactive molecules may be placed on raised elements; and a plurality of different reactive molecules may be placed within channel regions. Detection of reactions between the liquid and particular reactive molecules may be analyzed and test results may be provided.

Figure 1:
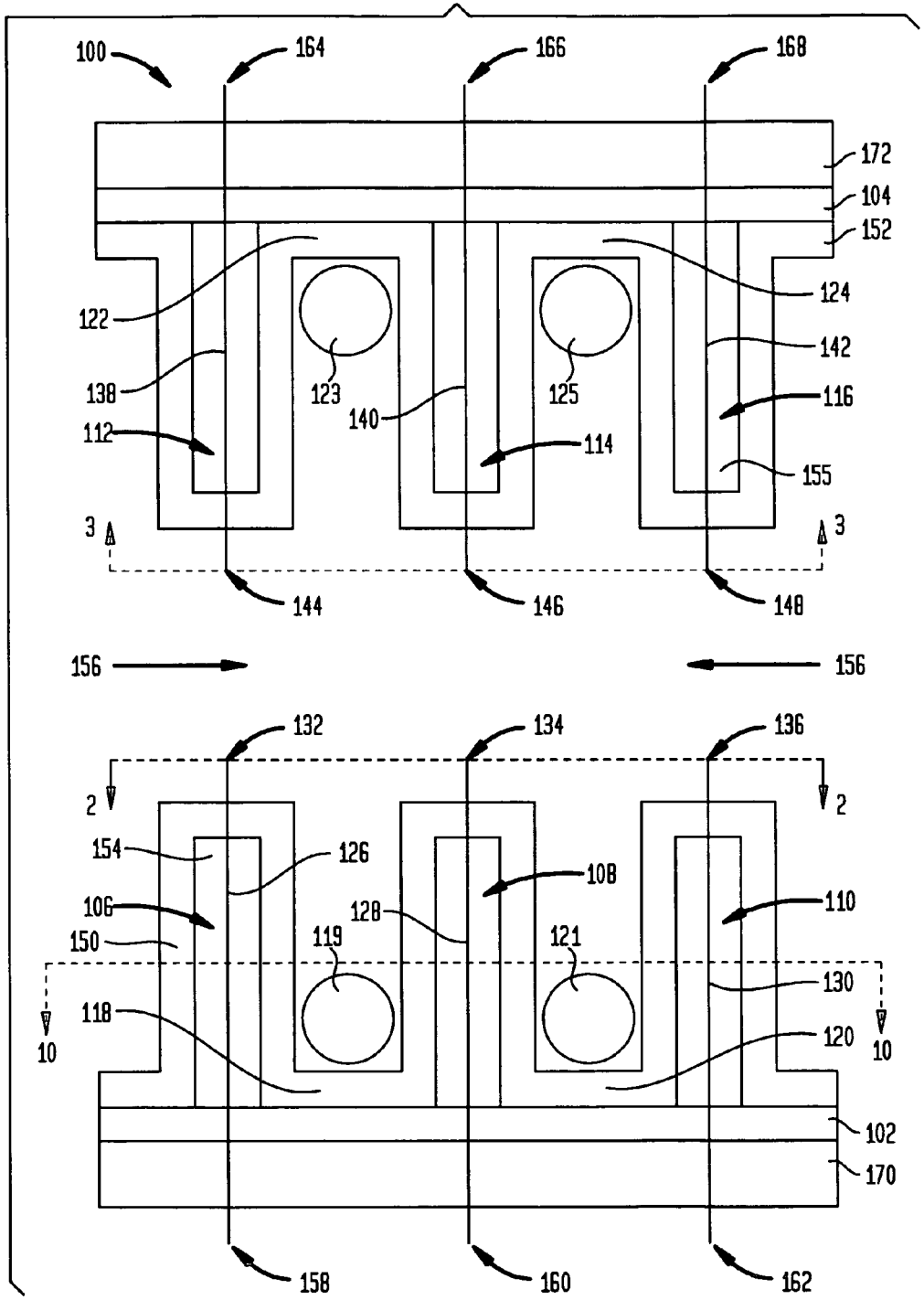
FIG. 1 shows a detection device.

FIG. 1 shows a detection device 100. The detection device 100 includes a first substrate 102 and a second substrate 104. A plurality of first raised elements 106, 108, and 110 may be on the first substrate 102. A plurality of second raised elements 112, 114 and 116 may be on the second substrate 104. The first raised elements 106, 108 and 110 may be mutually spaced apart by first channel regions 118 and 120 on the first substrate 102. The second raised elements 112, 114 and 116 may be mutually spaced apart by second channel regions 122 and 124 on the second substrate 104. The first raised elements 106, 108 and 110 respectively have first lateral surfaces 126, 128 and 130; and first distal ends 132, 134 and 136. The second raised elements 112, 114 and 116 respectively have second lateral surfaces 138, 140 and 142; and second distal ends 144, 146 and 148. FIG. 2, taken on line 2-2 in FIG. 1, shows first distal ends 132, 134 and 136, which may be included within a portion 200 of a first array. FIG. 3, taken on line 3-3 in FIG. 1, shows second distal ends 144, 146 and 148, which may be included within a portion 300 of a second array. It is understood that either of the first array portion 200 and second array portion 300 may be positioned over the other; or the first and second array portions may be horizontally positioned facing each other; or they may be oriented at any other angle to a level position, provided that they generally face each other. It is further understood that although the representative first distal ends 132, 134 and 136 and second distal ends 144, 146 and 148 are shown in FIGS. 1-3 as being positioned at a uniform planar distance from each other, such uniform distances are not required. Hydrophobic molecules 150 may be on first lateral surfaces 126, 128 and 130, first distal ends 132, 134 and 136, and first channel regions 118 and 120. Hydrophobic molecules 152 may be on second lateral surfaces 138, 140 and 142, second distal ends 144, 146 and 148, and second channel regions 122 and 124. A hydrophobic region 156 may be generated by the hydrophobic molecules 150 and 152 between the first array portion 200 and the second array portion 300.

Reactive molecules may be on the first raised elements 106, 108 and 110, including on the first distal ends 132, 134 and 136. Reactive molecules may be also on the second raised elements 112, 114 and 116, including on the second distal ends 144, 146 and 148. The reactive molecules may be reactive with specific organic or inorganic chemicals, polymers, or biological species. Such reactions may yield a reaction product having a moiety that is hydrophilic ("hydrophilic reaction products"). The reactive molecules on the first raised elements 106, 108 and 110 including on first distal ends 132, 134 and 136, will be referred to as primary reactive molecules. The reactive molecules on the second raised elements 112, 114 and 116 including on the second distal ends 144, 146 and 148, will be referred to as secondary reactive molecules.

The detection device 100 may include a system for controllably moving a hydrophilic liquid across the first array portion 200 and the second array portion 300 within the hydrophobic region 156. The hydrophilic liquid may be repelled by the hydrophobic molecules on the first distal ends 132, 134 and 136 and the second distal ends 144, 146 and 148. This repellency may minimize migration of the hydrophilic liquid past the first distal ends 132, 134 and 136 and the second distal ends 144, 146 and 148 until the hydrophobic state of the environment surrounding such molecules is reduced as described below.

In one example of an implementation, the first raised elements 106, 108, and 110 and the second raised elements 112, 114 and 116 may be conductors, and may be in communication at contact points 158, 160, 162, 164, 166 and 168 with external electric signal sources. In this example of an implementation, the raised elements may be surrounded by insulators 154 and 155 leaving only the distal ends 132, 134, 136, 144, 146 and 148 exposed to the hydrophobic region 156, and insulating the first lateral surfaces 126, 128 and 130 and the second lateral surfaces 138, 140 and 142.

In operation, electric signals may be selectively applied to the first distal ends 132, 134 and 136 and the second distal ends 144, 146 and 148, via the contact points 158, 160, 162, 164, 166 and 168. For example, application of an electric signal to distal end 132 may reduce the contact angle of a hydrophilic liquid with the distal end 132. A moderate reduction of the contact angle may effectively facilitate movement of the hydrophilic liquid toward or away from the distal end 132. Simultaneous application of an electric signal to second distal end 144 may accentuate this movement. Controlled application of such electric signals to distal ends may thus be employed to drive a hydrophilic liquid across the first array portion 200 and second array portion 300 within the hydrophobic region 156. An excessively strong electric signal may, however, cause localized conversion of the hydrophobic region 156 to a hydrophilic state, resulting in premature migration of the hydrophilic liquid beyond first distal ends such as first distal ends 132, 134 and 136; and beyond second distal ends such as second distal ends 144, 146 and 148.

In another example of an implementation, the first array and the second array respectively include first and second distal ends mutually spaced apart in a defined differential manner so as to constitute a density gradient of such distal ends. FIG. 4, taken on line 2-2 in a device having the same structure as device 100 in FIG. 1, shows a first array portion 400 according to this example of an implementation. FIG. 5, taken on line 3-3 in a device having the same structure as device 100 in FIG. 1, shows a second array portion 500 according to this example of an implementation. Referring to FIG. 4 for example, it can be seen that first distal ends 132, 133, 134 and 135 are spaced closely together, that first distal ends 136, 137, 139 and 141 are spaced farther apart, and that first distal ends 143, 145, 147 and 149 are spaced even farther apart. Since the first distal ends are hydrophobic, a hydrophilic liquid placed on the first array portion 400 on the closely spaced distal ends 132, 133, 134 and 135 will be repelled by these distal ends and seek a less hydrophobic environment by initially moving toward first distal ends 136, 137, 139 and 141, and subsequently moving toward first distal ends 143, 145, 147 and 149. Hence, the density gradient in the first array portion 400 may be used to induce a liquid to move in the direction of the arrow 405. Referring to FIG. 5, the density gradient in the second array portion 500 may likewise be used to induce a liquid to move in the direction of the arrow 502. The density gradients in the first array portion 400 and second array portion 500 may be mutually aligned so that the gradients in the directions of the arrows 405 and 502 induce a liquid to move in generally the same direction through the hydrophobic region 156.

Figure 6:
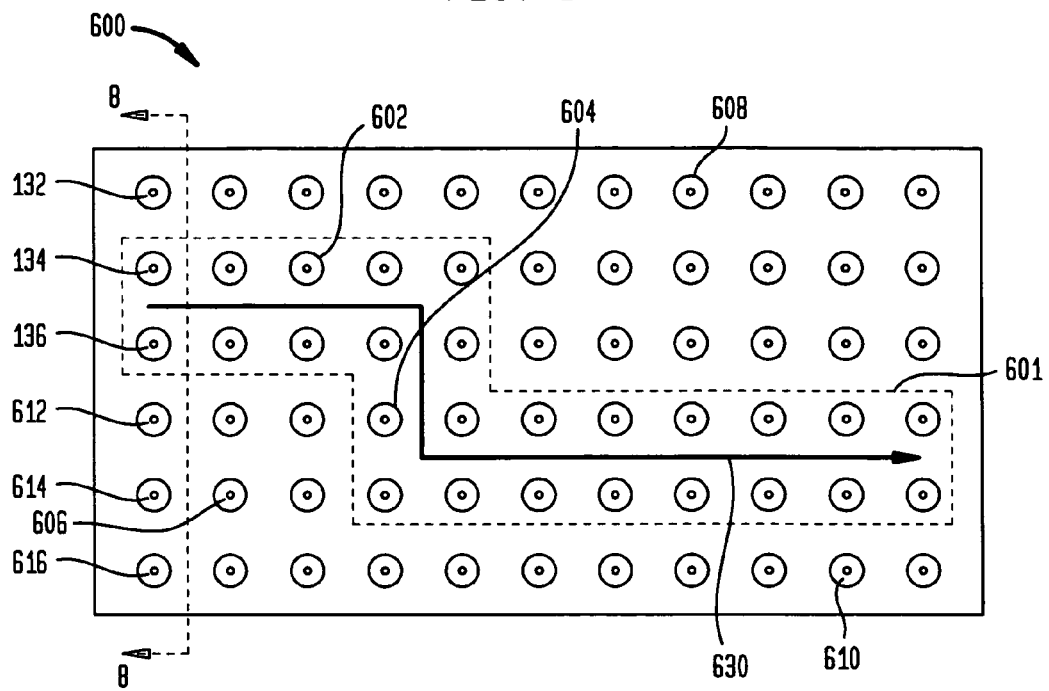
FIG. 6 shows a first array portion.
Figure 7:
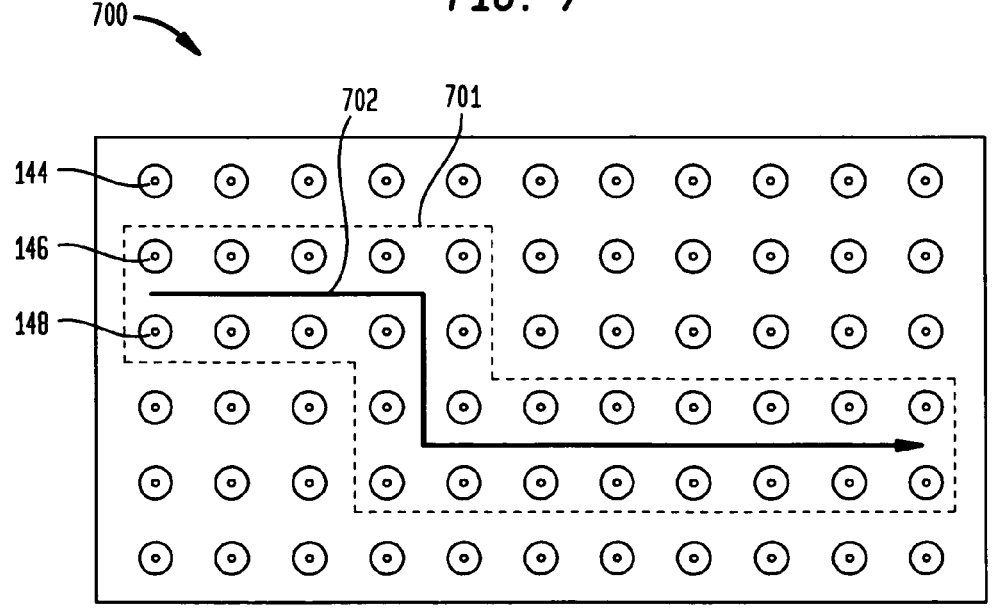
FIG. 7 shows a second array portion.

In an additional example of an implementation, the first array and the second array respectively include regions of first and second distal ends having relatively decreased hydrophobicity, defining a pathway across the respective arrays. FIG. 6, taken on line 2-2 in a device having the same structure as device 100 in FIG. 1, shows a first array portion 600 according to this example of an implementation. FIG. 7, taken on line 3-3 in a device having the same structure as device 100 in FIG. 1, shows a second array portion 700 according to this example of an implementation. Referring to FIG. 6 for example, a plurality of first distal ends within the dotted line 601 including representative first distal ends 134, 136, 602 and 604 have relatively lower hydrophobicity than do a plurality of first distal ends outside the dotted line 601 including representative first distal ends 132, 606, 608 and 610. A hydrophilic liquid placed on the first array portion 600 will tend to flow over the first distal ends having relatively lower hydrophobicity including representative first distal ends 134, 136, 602 and 604, as the first distal ends having relatively higher hydrophobicity more strongly repel the hydrophilic liquid. Hence, the relatively lower hydrophobicity of the indicated first distal ends in the first array portion 600 may be used to induce a liquid to flow over a path in the direction of the arrow 630. Referring to FIG. 7, the second distal ends having relatively lower hydrophobicity within the dotted line 701 in the second array portion 700 may likewise be used to induce a liquid to flow over a path in the direction of the arrow 702. The distal ends with relatively lower hydrophobicity in the first array portion 600 and second array portion 700 may be mutually aligned so that lower hydrophobicity along paths in the directions of the arrows 630 and 702 induces a liquid to flow generally on the same pathway through the hydrophobic region 156. Pressure applied laterally into the hydrophobic region 156 may then be used to push a hydrophilic liquid to flow on a path in the direction of the arrows 630 and 702.

Figure 8:
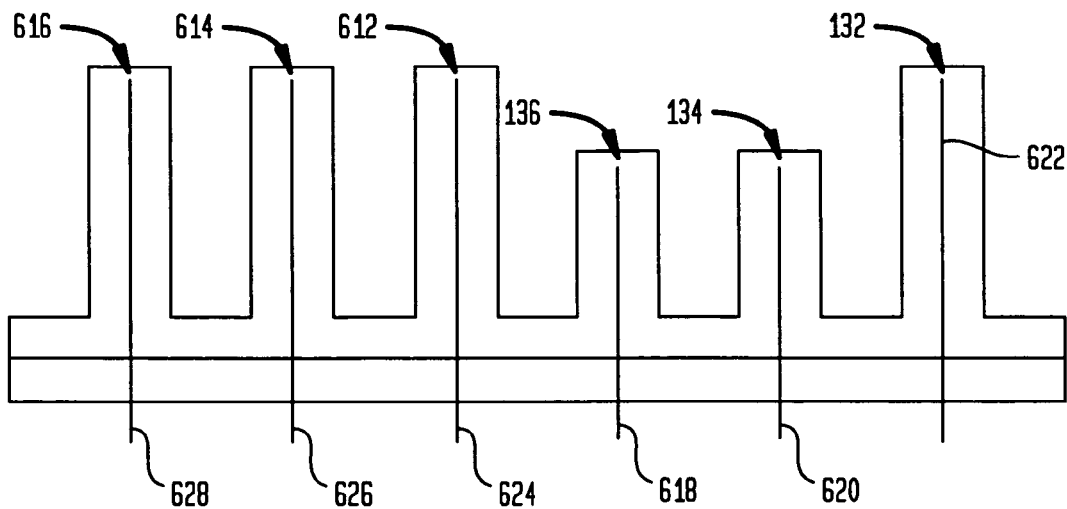
FIG. 8 shows first distal ends also shown in FIG. 6.

In a further example of an implementation also illustrated by FIGS. 6 and 7, the first array portion 600 and the second array portion 700 may respectively include regions of first and second distal ends having relatively short lateral surfaces, defining a pathway across the respective arrays. As an example, the raised elements within the first and second array portions may be in the form of nanograss blades. The term "nanograss" includes an array of blade-shaped raised elements having dimensions on a nanometer scale that are distributed on a substrate, having an appearance under magnification similar to that of a grass lawn. In such an example of an implementation, nanograss blades which are relatively short have such relatively short lateral surfaces. Referring to FIG. 1, as an example, the lateral surface 128 of raised element 108 may be shorter than the lateral surfaces 126 and 130 of raised elements 106 and 110, respectively. Referring to FIG. 1 as an example, the lateral surface 140 of raised element 114 may be shorter than the lateral surfaces 138 and 142 of raised elements 112 and 116, respectively. FIG. 6, taken on line 2-2 in a device having the same structure as device 100 in FIG. 1, shows the first array portion 600 according to this example of an implementation. FIG. 7, taken on line 3-3 in a device having the same structure as device 100 in FIG. 1, shows the second array portion 700 according to this example of an implementation. Referring to FIG. 6 for example, a plurality of first distal ends within dotted line 601 including representative first distal ends 134, 136, 602 and 604 have relatively shorter lateral sides than may a plurality of first distal ends outside dotted line 601 including representative first distal ends 132, 606, 608 and 610. FIG. 8 taken on line 8-8 shown in FIG. 6 further illustrates first distal ends 134 and 136 within dotted line 601 in FIG. 6, and first distal ends 132, 612, 614 and 616 outside dotted line 601 in FIG. 6. It can be seen in FIG. 8 that the lateral sides 618 and 620 of the first distal ends 136 and 134 are shorter than the lateral sides 622, 624, 626 and 628 of the first distal ends 132, 612, 614 and 616. Since the first distal ends are hydrophobic, a hydrophilic liquid placed on the first array portion 600 will tend to flow over the first distal ends having relatively short lateral sides including representative first distal ends 134, 136, 602 and 604, as the shorter lateral sides leave more space between such distal ends and the second array portion 700. Hence, the shorter lateral sides of such first distal ends in the first array portion 600 may be used to induce a liquid to flow over a path in the direction of the arrow 630. Referring to FIG. 7, the second distal ends having relatively short lateral sides in the second array portion 700 may likewise be used to induce a liquid to flow over a path in the direction of the arrow 702. The raised elements with relatively short lateral sides in the first array portion 600 and second array portion 700 may be mutually aligned so that a liquid is induced to flow generally on a pathway along arrows 630 and 702 through the hydrophobic region 156. Pressure applied laterally into the hydrophobic region 156 may then be used to push a hydrophilic liquid to flow on a path in the direction of the arrows 630 and 702. In another example of an implementation, first and second distal ends having lower hydrophobicity, as discussed in the previous example, may also be included.

In another example of an implementation, aspect ratios of the first and second distal ends may be selected. For example, changing the shapes of distal ends may effectively change the hydrophobicity of the first and second arrays. A smaller contact area of hydrophobic moieties may effectively be a less hydrophobic environment for an adjacent droplet of hydrophilic liquid. Distal ends may, for example, be pointed, sawtoothed, flat-topped, rounded, or bowl-shaped. Distal ends and raised elements may also have a variety of profiles, such as square, triangular, round, elliptical, or polygonal. In another example of an implementation, a plurality of raised elements may be integrated to form a distal end shaped as a line or a honeycomb pattern or the like. As examples, raised elements may be shaped as posts, plates, lines, or closed cells.

In one example of one implementation, a pitch between a plurality of first distal ends or second distal ends may be defined. Pitch is an average distance between adjacent distal ends of raised elements on a substrate. As an example, the average pitch between first distal ends may be less than about 50 microns. In another example of an implementation, the average pitch between second distal ends may be within a range of between about 50 nanometers and about 50 microns. As a further example, the average pitch between first distal ends may be within a range of between about 100 nanometers and about 10 microns. In one example of one implementation, less than about 25% of a bottom surface of a droplet of hydrophilic liquid may be in contact with adjacent distal ends of an array. As another example, less than about 10% or less than about 3% of such a bottom surface may be in such contact.

In one example of one implementation, a hydrophilic liquid may be placed in the hydrophobic region 156 in the form of an individual droplet. For example, a plurality of individual droplets of hydrophilic liquid may be introduced into the hydrophobic region in a spaced apart, controlled manner. In one example of one implementation, the first raised elements 106, 108, and 110 and the second raised elements 112, 114 and 116 include conductors as earlier discussed, and external electric signals may be applied in a controlled manner to such raised elements to coax individual droplets of the hydrophilic liquid out of a reservoir placed adjacent to the hydrophobic region. In another example of an implementation, a continuous flow of the hydrophilic liquid may be directed into the hydrophobic region 156.

Figure 9:
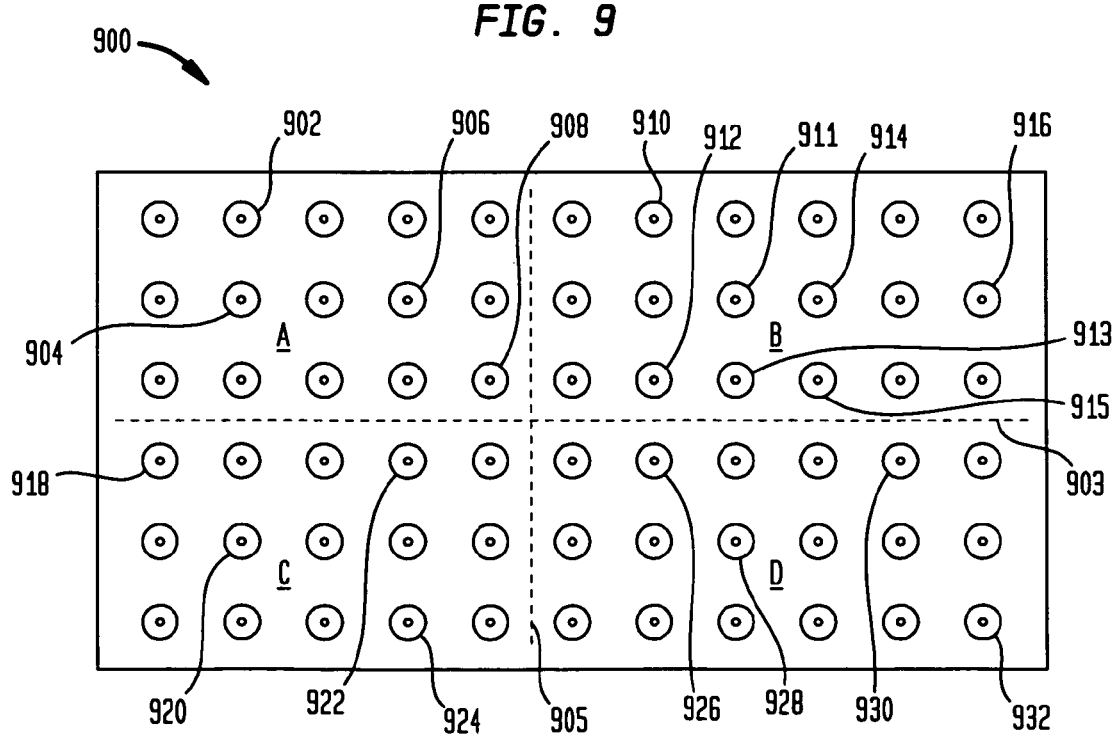
FIG. 9 shows a first array portion.

FIG. 9 is taken on line 2-2 in a device having the same structure as device 100 in FIG. 1. FIG. 9 shows an example of an implementation of a first array portion 900 of first distal ends. The first array portion 900 includes a plurality of different primary reactive molecules on the first raised elements, clustered into four groups A, B, C and D delineated by dotted lines 903 and 905. In this example of an implementation, a group of first raised elements including raised elements having representative distal ends 902, 904, 906 and 908, have primary reactive molecule A on the raised elements; another group of first raised elements including representative first distal ends 910, 912, 914 and 916 have primary reactive molecule B on those raised elements; a further group of first raised elements including representative first distal ends 918, 920, 922 and 924 have primary reactive molecule C on those raised elements; and an additional group of first distal ends including representative first distal ends 926, 928, 930 and 932 have primary reactive molecule D on those raised elements. A second array portion facing the first array portion in the manner as discussed with respect to FIGS. 1 and 3 may have a plurality of different secondary reactive molecules on second raised elements in a likewise manner. A hydrophilic liquid introduced into the hydrophobic region 156 may flow across the first array portion 900; and across a corresponding second array portion having the form of the second array portion 300 shown in FIG. 3 and discussed in connection with FIG. 1.

A component of the hydrophilic liquid may then selectively react with one, more than one, or none of the primary reactive molecules A, B, C and D, depending on the molecular structures of the primary reactive molecules and of the components of the hydrophilic liquid. For example, a component of the hydrophilic liquid may selectively react with primary reactive molecule B. In this case, the hydrophobicity of representative first distal ends 910, 912, 914 and 916 may be affected by this selective reaction. For example, the hydrophobicity of the hydrophobic region 156 in the vicinity of representative first distal ends 910, 912, 914 and 916 may be reduced. This localized reduction in hydrophobicity may induce the hydrophilic liquid to wet one or more of the first distal ends 910, 912, 914 and 916, and descend to a channel region such as representative channel region 118 of the device 100.

In one example of an implementation, the localized descent of a hydrophilic liquid to representative channel region 118 of the device 100 may be detected. For example, referring to FIG. 1, a detector 170 may be positioned adjacent to the first substrate 102. The detector 170 may, for example, detect changes in transmission of light through the first substrate 102. As an example, the detector 170 may be a light detector.

The detector 170 may further be capable of identifying a position of such detected light in relation to a position within the first array portion 900. In this manner, the specific reaction of a component of the hydrophilic liquid with the primary reactive molecule B may be detected. This detected reaction constitutes data that may then be further analyzed to provide information, such as a test result for example. A detector 172 may likewise be positioned adjacent to the second substrate 104.

Figure 10:
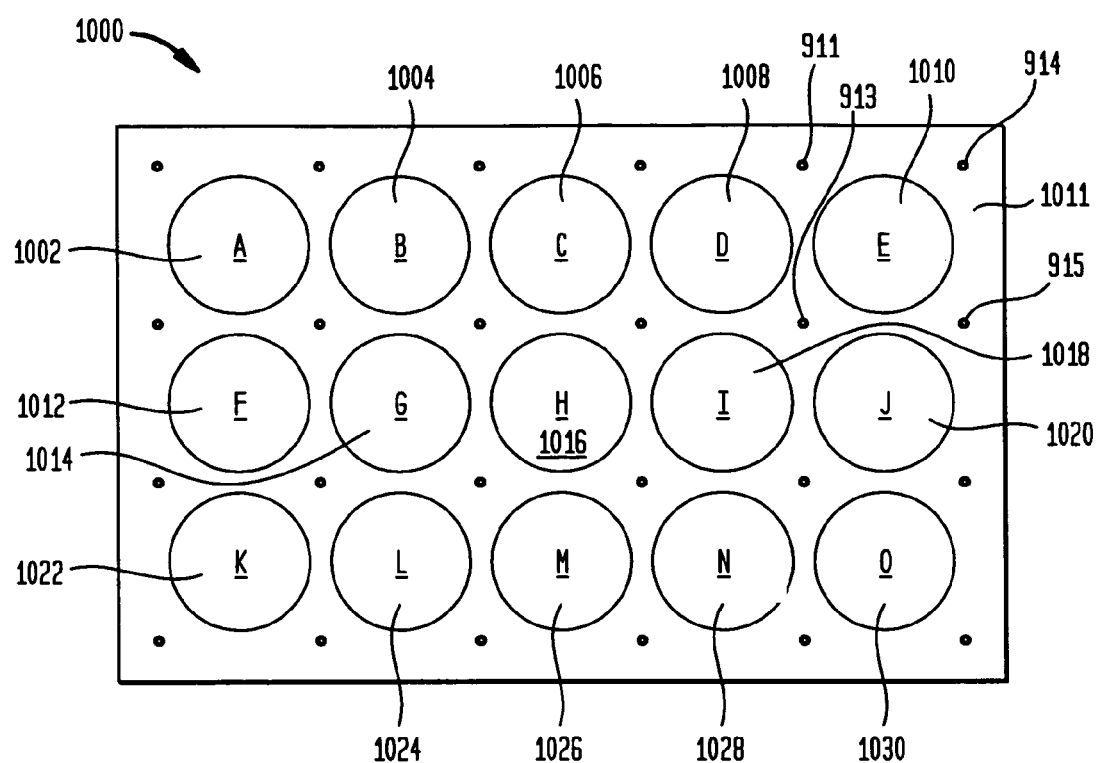
FIG. 10 shows a third array portion.

In one example of an implementation, a plurality of different primary reactive molecules may be located on microspheres placed in first channel regions having the same structure as representative first channel regions 118 and 120 shown in FIG. 1. FIG. 10, taken on line 10-10 shown in FIG. 1 in a device having the same structure as device 100, shows an example of an implementation of a third array portion 1000 of microspheres placed in first channel regions. The third array portion 1000 includes a plurality of different primary reactive molecules on the microspheres. In this example of an implementation, microspheres may be selected having diameters scaled approximately to the dimensions of the first channel regions, so that one microsphere may be of sufficient size to substantially cover that portion of the substrate 102 that is within a first channel region. It will be understood that spheres having sizes of other magnitudes, or non-spherical particles, may also be used. In this example of an implementation, each of microspheres 1002, 1004, 1006, 1008, 1010, 1012, 1014, 1016, 1018, 1020, 1022, 1024, 1026, 1028 and 1030 has a plurality of primary reactive molecules A, B, C, D, E, F, G, H, I, J, K, L, M, N, and O respectively on it. Each of the primary reactive molecules A-O may be different in chemical or biological structure and reactivity.

In operation, a hydrophilic liquid introduced into the hydrophobic region 156 may flow across the first array portion 900 and the corresponding second array portion 300 as shown for example in FIG. 3 and discussed in connection with FIG. 1. A component of the hydrophilic liquid may then selectively react with one, more than one, or none of the primary reactive molecules A, B, C and D on the raised elements, depending on the molecular structures of the primary reactive molecules and of the components of the hydrophilic liquid. The hydrophobicity of representative first distal ends 910, 912, 914 and 916, for example, may then be reduced by such a reaction, so that the hydrophobicity of the hydrophobic region 156 in the vicinity of first distal ends 910, 912, 914 and 916 may also be reduced. This localized reduction in hydrophobicity may induce the hydrophilic liquid to wet one or more of the first distal ends 910, 912, 914 and 916, and descend to a channel region such as channel region 1011 defined by the four raised elements having distal ends 911, 913, 914 and 915. Channel region 1011 may, for example, contain microsphere 1010, which has a plurality of reactive molecules E on it. Depending on the structure of reactive molecules E and of components in the hydrophilic liquid, a reaction between them may or may not occur.

In one example of an implementation, a reaction between reactive molecules E and a component of the hydrophilic liquid may be detected. For example, a detector 170 as earlier discussed may be positioned adjacent to a first substrate having the same structure as the first substrate 102. In addition to detecting changes in transmission of light through the first substrate, the detector 170 may also distinguish between different types of light. For example, the detector may be able to identify a wavelength of such light. In addition, the detector may be able to distinguish among various types of light, such as transmitted light and fluorescence. The detector may further, for example, be able to detect radioactivity such as may be emitted by radioactive isotopes in a chemical or biological molecule that is located in a channel region. The detector 170 may also be capable of identifying a position of such detected light or radioactivity in relation to a position within the first array portion 900. In this manner, the specific reaction of a component of the hydrophilic liquid with the reactive molecule E may be detected. This detected reaction constitutes data that may then be further analyzed to provide information, such as a test result.

In another example of an implementation, a detector 170 may be able to detect both the specific reaction of a component of the hydrophilic liquid with the primary reactive molecule B on raised elements, and the specific reaction of a component of the hydrophilic liquid with the reactive molecule E within channel regions. These detected reactions both constitute data that may then be further analyzed.

The composition of the hydrophilic liquid that is utilized depends on the particular analysis to be carried out using the device 100. The hydrophilic liquid and its components constitute a test sample to be subjected to analysis by the device 100. For example, the hydrophilic liquid may include biological or chemical components about which an analysis is to be carried out such as structural identification, property determination, prior conversion from one state or structure into another, deterioration, contamination, prior reaction, or some other analysis. For example, components of the hydrophilic liquid may include biologically active monomers or polymers such as amino acids, polynucleotides, proteins, carbohydrates, fats, ribonucleic acids (RNA), and deoxyribonucleic acids (DNA). By "DNA" and "RNA" are broadly meant all forms of ribonucleic and deoxyribonucleic acids and portions thereof, including for example, messenger RNA and complementary DNA, without limitation. In one example of an implementation, components of the hydrophilic liquid include single-stranded DNA or RNA macromolecules or portions of the same, which may have been specifically prepared and isolated for purposes of carrying out specific binding reactions using the device 100. Further for example, components of the hydrophilic liquid may include other chemical species such as pharmaceutically active compounds, herbicides, pesticides, heavy metals, environmental pollutants, polyelectrolytes, or any other chemical monomers, oligomers or polymers of natural or man-made origin that are of interest. Polystyrene bound on raised elements, for example, may swell in the presence of toluene and may then allow the toluene to migrate away from the hydrophobic region 156. Polyvinylpyrrolidone (PVP) bound on raised elements may form complexes with heavy metals. Hence, the presence of heavy metals may cause PVP to swell, changing the environment to a hydrophilic state and allowing liquid containing the heavy metals to migrate away from the hydrophobic region 156 toward channel region 118, 120, 122 or 124. Some of these interactions may be pH-dependent. In general, the liquid to be analyzed may be sufficiently hydrophilic to minimize its premature migration away from the hydrophobic region 156 beyond the first and second distal ends of the raised elements. Further, the hydrophilic liquid may have a fluid consistency that may generally be capable of being induced to flow across the first and second arrays.

The compositions of the primary and secondary reactive molecules may be selected based on the structures and known or potential reactivity of those components of the hydrophilic liquid that are to be studied. For example, where identification of a single stranded DNA or RNA macromolecule or a portion of same is to be carried out, a complementary single stranded polynucleotide may be isolated or synthesized and employed as the primary and secondary reactive molecules. The resulting reaction product may be designed to have a hydrophilic moiety. In one example of an implementation, a plurality of different single stranded polynucleotides may be placed on raised elements including first and second distal ends in a controlled and defined manner, so that the locations of reactions detected between such primary and secondary reactive molecules with components of the hydrophilic liquid may be indicative of information about the structure of such components. In another example of an implementation for the analysis of DNA or RNA in a hydrophilic liquid, suitable antibodies may be placed on first and second raised elements, including distal ends, in a controlled and defined manner. Fluorescent markers and their quenchers, for example, may then be used to detect the presence or absence of specific binding reactions between the antibodies and a target DNA or RNA sequence. Further for example, where identification of a protein or a portion of a protein is to be carried out, a suitable antibody may be isolated and employed as the primary and/or secondary reactive molecules. In one example of an implementation, a plurality of different antibodies may be placed on first and second distal ends of raised elements in a known and defined manner, so that the locations of reactions detected between such primary and secondary reactive molecules with components of the hydrophilic liquid may be indicative of information about the structure of such components. In one example of an implementation, the compositions of the primary and secondary reactive molecules on the raised elements may be selected to provide information, regarding components of the hydrophilic liquid, that may be different from and supplemental to the information provided by detection of reactions between such components and the primary and secondary reactive molecules within the channel regions.

In an example of an implementation, the first substrate 102 may be a membrane. By "membrane" is broadly meant a body having pores passing through it, such that some materials may selectively pass through the body. The materials that selectively pass through the body may be in a liquid, solid, or gaseous state, or any combination. The pores may have any size range or distribution suitable to permit a material to selectively pass through the substrate 102. In one example of an implementation, a portion of a hydrophilic liquid reaching a channel region of the first substrate 102 may pass through the first substrate 102 and be directed elsewhere for further analysis.

In another example of an implementation, the hydrophobic molecules 150 on first lateral surfaces 126, 128 and 130, first distal ends 132, 134 and 136, and first channel regions 118 and 120 may be chosen to provide a repellent force against migration of the hydrophilic liquid. In a further example of an implementation, the hydrophobic molecules 152 on second lateral surfaces 138, 140 and 142, second distal ends 144, 146 and 148, and second channel regions 122 and 124 may be chosen to provide a repellent force against migration of the hydrophilic liquid.

In one example of an implementation, the device 100 includes first substrate 102 overlaid by second substrate 104, so that gravity pulls the hydrophilic liquid downward toward the first substrate 102. In another example of an implementation, the hydrophobicity of the hydrophobic molecules 150 may be stronger or weaker than the hydrophobicity of the hydrophobic molecules 152. As an example, the hydrophobic molecules 150 and 152 may have the same or different molecular structures. In one example of an implementation, the hydrophobic molecules 150 and 152 may include fluorinated compounds. In another example of an implementation, the hydrophobic molecules 150 and 152 may include fluoropolymers.

In one example of an implementation, the first substrate 102 and the second substrate 104 may be each in the form of substantially flat plates as shown in FIGS. 1-3. In further example of an implementation, the first substrate 102 and second substrate 104 may have other mutually conformed forms, such as concentric tubes, or other non-planar mutually conforming surfaces.

Further modifications of the implementations discussed above are contemplated. For example, the second substrate and second raised elements may be omitted. In another example of an implementation, arrays in addition to first and second arrays may be mutually positioned to define a hydrophobic region between them. In another example of an implementation, more than one system or more than one type of system for controllably moving a liquid across the arrays may be provided, or different systems may be selected for use respectively with the first and second arrays. In a further example of an implementation, reactive molecules may be bound to solid substrates other than spheres, or may be directly bound to the channel regions of the device 100.

Figure 11:
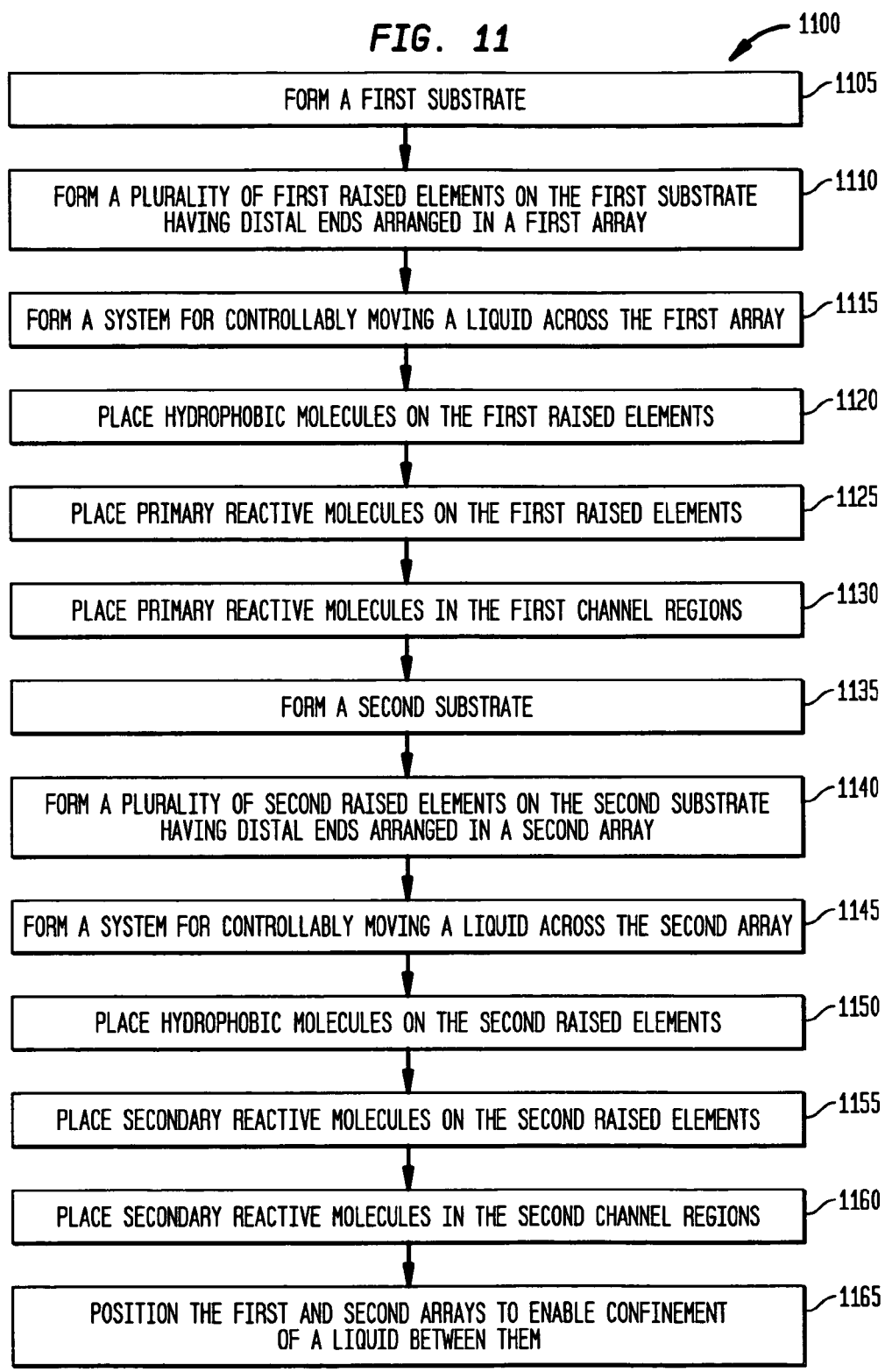
FIG. 11 shows a process for fabricating the device shown in FIG. 1.

FIG. 11 shows a process 1100 for fabricating the device 100 shown in FIG. 1. The process may begin with formation of a first substrate 102 in step 1105. In one example of an implementation the first substrate may be a body of a solid material such as a ceramic or polymer. As an example, the first substrate 102 may be an electrical insulator.

In step 1110, a plurality of first raised elements such as raised elements 106, 108 and 110 may be formed on the first substrate 102. The raised elements may be arranged so as to be mutually spaced apart by channel regions, for example channel regions 118 and 120, and the first distal ends collectively form a first array portion 200. In one example of an implementation, the raised elements may take a form as disclosed in Joanna Aizenberg et al., U.S. patent application Ser. No. 10/999,249, entitled "Reversibly Adaptive Rough Micro- and Nano-Structures", filed on Nov. 30, 2004, which is hereby incorporated herein by reference in its entirety.

In step 1115, a system may be formed for controllably moving a liquid across the first array. In one example of an implementation, this system may be formed by fabricating distal ends, such as distal ends 132, 134 and 136, as conductors, and placing the distal ends in communication with conductors 158, 160 and 162 respectively. In this example of an implementation, the raised elements 106, 108 and 110 may be protected by insulators 154, formed of, for example, silicon dioxide. In an additional example of an implementation, such a system may be formed by arranging the first array in a defined density gradient of the distal ends of the raised elements such as distal ends 132-149 as shown in FIG. 4 discussed above. In a further example of an implementation, such a system may be formed by arranging a channel of distal ends of raised elements having relatively reduced hydrophobicity as discussed above in connection with FIG. 6. In another example of an implementation, such a system may be formed by arranging a channel of distal ends having shortened lateral surfaces as discussed above in connection with FIGS. 6 and 8. In an example of an implementation, steps 1110 and 1115 may be carried out simultaneously.

In step 1120, hydrophobic molecules 150 may be placed on the distal ends such as distal ends 132, 134 and 136. In one example of an implementation, hydrophobic molecules may be also placed on the lateral surfaces 126, 128 and 130, and in the channel regions 118 and 120. For example, hydrophobic molecules may be included in a coating composition which may then be applied to the device 100.

In step 1125, primary reactive molecules as earlier discussed may be placed on raised elements including the distal ends 132, 134 and 136. In one example of an implementation, a plurality of selected reactive molecules may be placed on a stamp such as a polydimethylsulfoxide (PDMS) stamp, which may then be brought into contact with the distal ends 132, 134 and 136. In another example of an implementation, a plurality of reactive molecules may be distributed in an array of wells in a known manner, and each of distal ends 132, 134 and 136 may then be dipped into a well to apply reactive molecules. In a further example of an implementation, a droplet containing a reactive molecule may be positioned over a first distal end by use of a system for applying external electric signals to the first array as earlier discussed, and may then be allowed to react with and bond to the first distal end.

Bonding of primary reactive molecules on the first raised elements may be induced by selecting a known binding pair system. For example, biologically active materials may be attached to a surface by binding a biotin moiety to the biologically active material and then binding streptavidin to the surface, or vice versa. When biotin and streptavidin are brought together, they reversibly bind. In another example of an implementation, the complementary binding properties of nucleotides may be used. Specific binding reactions between antibodies and proteins or ribonucleic acids may be used. Any of the classic organic condensation reactions may be used, such as binding reactions between carboxylic acids with amines or alcohols; amines with epoxides; and sol-gels with silanes. In one example of an implementation, a distal reactive material in the form of an elongated molecule may be bound onto a raised element with a specifically reactive moiety dangling at its unbound end. In another example of an implementation, primary reactive molecules may be bound onto raised elements as self-aligned monolayers (SAMs).

In step 1130, primary reactive molecules, as earlier discussed, may be placed in the channel regions 118 and 120. In one example of an implementation, primary reactive molecules may be bound onto spheres each having dimensions suitable to substantially cover a portion of the substrate 102 defined by a channel region 118 or 120. Such spheres may then be placed in the channel regions in a controlled and known manner, so that the identities for the primary reactive molecules on a given sphere in a given location of a third array portion may be known as shown in FIG. 10. In one example of an implementation, representative channel region 118 may be individually rendered temporarily hydrophilic by application of an electric signal to distal end 132 and/or 134, so that a hydrophilic solution of spheres bound with a particular known primary reactive molecule may be directed into the hydrophobic region 156 resulting in the deposit of a sphere 119 into channel region 118. Movement of the spheres may be induced, for example, by sonication. A sphere 121 may then be placed in the channel region 120. Additional spheres bound with other primary reactive molecules may likewise by placed in other channel regions.

In step 1135, a second substrate 104 may be formed. In step 1140 a plurality of second raised elements 144, 146 and 148 may be formed on a second substrate 104 in the form of a second array portion 300. In step 1145, a system may be formed for controllably moving a liquid across the second array portion 300. In step 1150, hydrophobic molecules may be placed on the second distal ends 144, 146 and 148, and may also be placed on the corresponding lateral surfaces 138, 140 and 142, and in the channel regions 122 and 124. In step 1155, secondary reactive molecules may be placed on the second distal ends 144, 146 and 148, and may also be placed on the corresponding lateral surfaces 138, 140 and 142, and in the channel regions 122 and 124. In step 1160, secondary reactive molecules bound on spheres 123 and 125 may be placed in channel regions 122 and 124. These steps may be carried out in the same manners as discussed with respect to steps 1105-1130.

In step 1165, the first array portion 200 and second array portion 300 may be positioned to enable confinement of a hydrophobic liquid between them. In one example of an implementation, the first substrate 102 and the second substrate 104 may be in the form of substantially planar plates. In this example of an implementation, the second substrate 104 may be placed over the first substrate 102 in a spaced apart manner so that the distal ends 132, 134, and 136 face the distal ends 144, 146 and 148 over a suitable distance.

Further modifications of the process 1100 as discussed above are contemplated. In one example of an implementation, steps 1135-1160 may be omitted. In another example of an implementation, steps 1135-1160 may be repeated for the formation of a third or subsequent substrate. In another example of an implementation, steps 1105 and 1110 may be carried out in an integral process of forming a structure including raised elements. In additional example of an implementation, the order of steps may be changed. For example, primary reactive molecules may be placed in the first channel regions before primary reactive molecules are placed on the raised elements including the first distal ends. Further for example, hydrophobic molecules and primary reactive molecules may be simultaneously placed on the raised elements.

Figure 12:
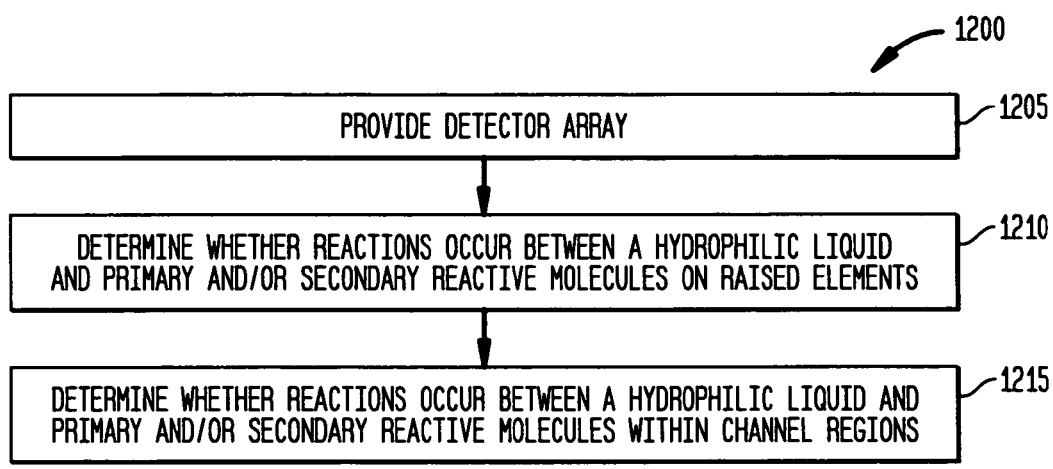
FIG. 12 shows a method for using the device shown in FIG. 1.

FIG. 12 shows a method 1200 for using the device 100 shown in FIG. 1. The method may begin in step 1205 with providing a device 100 as discussed above and fabricated, as an example, as described in connection with FIG. 11. The device 100 includes first raised elements having first distal ends on a first substrate, mutually spaced apart by first channel regions. Hydrophobic molecules may be provided on raised elements including first distal ends. Primary reactive molecules may be provided on first raised elements. Primary reactive molecules may be provided in first channel regions. Second raised elements having second distal ends may be provided on a second substrate, mutually spaced apart by second channel regions. Hydrophobic molecules may be provided on second raised elements. Secondary reactive molecules may be provided on second raised elements. Secondary reactive molecules may be provided in second channel regions.

In step 1210, a determination may be made as to whether reactions have occurred between primary and secondary reactive molecules on raised elements and a hydrophilic liquid. The hydrophilic liquid may be introduced into the device 100 as discussed above in connection with FIGS. 1-3. The determination as to whether reactions have occurred between primary and secondary reactive molecules on raised elements and a hydrophilic liquid depends on the structure and reactivity of the molecules and components of the hydrophilic liquid.

In step 1215, a determination as to whether reactions have occurred between primary and secondary reactive molecules within channel regions and a hydrophilic liquid is made. This determination likewise depends on the structure and reactivity of the molecules and components of the hydrophilic liquid. Considerations regarding such structure and reactivity relationships were earlier discussed.

In one example of an implementation where both steps 1210 and 1215 are carried out, the reactive molecules on the raised elements and the reactive molecules in the channel regions may be selected to efficiently provide test results. For example, reaction of components of the hydrophilic liquid with reactive molecules on the raised elements may serve as a pre-screening test to minimize the frequency of exposures of the reactive molecules in the channel regions to potential reactions with components of the hydrophilic liquid. In one example of an implementation, reactive molecules on the raised elements may specifically bind hemoglobin, and reactive molecules in the channel regions may specifically bind iron. In this manner, tests for the presence of iron in hemoglobin may be only carried out in channel regions localized where hemoglobin may be present in a hydrophilic liquid that may be induced to flow over first and second arrays of distal ends of raised elements.

We claim:

1. A device, comprising: a first substrate; a plurality of first raised elements on the first substrate, the first raised elements mutually spaced apart by first channel regions on the first substrate, each of the first raised elements having a first lateral surface and a first distal end, the first distal ends being hydrophobic and forming a first array; hydrophobic molecules on the first lateral surfaces and on the first distal ends; and primary reactive molecules located on the first distal ends for generating hydrophilic reaction products, the primary reactive molecules being capable of reacting with a chemical or biological component of a liquid to decrease a hydrophobicity of the first distal ends.

2. The device of claim 1, including: a second substrate; a plurality of second raised elements on the second substrate, the second raised elements mutually spaced apart by second channel regions on the second substrate, each of the second raised elements having a second lateral surface and a second distal end, the second distal ends being hydrophobic and forming a second array, the first and second arrays being spaced apart and facing toward each other to enable confinement of a liquid between the arrays; hydrophobic molecules on the second lateral surfaces and on the second distal ends; and secondary reactive molecules located on the second distal ends for generating hydrophilic reaction products, the secondary reactive molecules being capable of reacting with a chemical or biological component of a liquid to decrease a hydrophobicity of the second distal ends.

3. The device of claim 1, including a system for controllably moving a liquid across the first array.

4. The device of claim 3, wherein the system for controllably moving a liquid across the first array includes a pathway collectively formed by a plurality of the first raised elements having first distal ends being less hydrophobic than the first distal ends of others of the first raised elements.

5. The device of claim 3, wherein the system for controllably moving a liquid across the first array includes a pathway collectively formed by a plurality of the first raised elements having first lateral surfaces extending over shorter lengths away from the first substrate than lengths of first lateral surfaces of others of the first raised elements extending away from the first substrate.

6. The device of claim 1, wherein the primary reactive molecules include: a first plurality of the primary reactive molecules located on the first distal ends of the first raised elements within a first portion of the first array, and a second plurality of the primary reactive molecules having a different structure than the first plurality of the primary reactive molecules and being located on the first distal ends of the first raised elements within a second portion of the first array.

7. The device of claim 1, wherein primary reactive molecules are located on spheres within the first channel regions.

8. The device of claim 7, wherein the primary reactive molecules located on the spheres include: a first of the primary reactive molecules being located on a first of the spheres; and a second of the primary reactive molecules being located on a second of the spheres and having a different structure than the first of the primary reactive molecules located on the first of the spheres.

9. The device of claim 8, wherein the spheres form a third array, the first of the spheres having a first location within the third array, and the second of the spheres having a second location within the third array.

10. The device of claim 7, wherein the primary reactive molecules located on each, of a plurality of the spheres respectively have different known reactivities with specific organic or inorganic chemicals, polymers, or biological species being components of a liquid; and wherein the primary reactive molecules on each of the plurality of the spheres are selected from a group consisting of chemically reactive molecules and biologically reactive molecules.

11. The device of claim 1, including a light detector for detecting light through a portion of the first substrate.

12. The device of claim 1, wherein the first raised elements are arranged in a variable pitch on the first substrate, defining a density gradient of the first distal ends in the first array.

13. The device of claim 1, wherein the first substrate is a microporous membrane.

14. The device of claim 1, wherein the primary reactive molecules respectively located on each of a plurality of the first distal ends respectively have different known reactivities with specific organic or inorganic chemicals, polymers, or biological species being components of a liquid; and wherein the primary reactive molecules on each of the plurality of the first distal ends are selected from a group consisting of chemically reactive molecules and biologically reactive molecules.

15. The device of claim 1 wherein the primary reactive molecules respectively located on each of a plurality of the first distal ends respectively have different structures, and wherein the primary reactive molecules respectively having each of the different structures are capable of selectively reacting with a different chemical or biological component of a liquid to decrease the hydrophobicity of the plurality of the respective first distal ends.

16. The device of claim 1 wherein the chemical or biological component, with which the primary reactive molecules on the first distal ends are capable of reacting to decrease the hydrophobicity of the first distal ends, includes a member selected from a group consisting of biologically active monomers and biologically active polymers.

17. The device of claim 1 wherein the chemical or biological component, with which the primary reactive molecules on the first distal ends are capable of reacting to decrease the hydrophobicity of the first distal ends, includes a member selected from a group consisting of amino acids, polynucleotides, ribonucleic acids, deoxyribonucleic acids, proteins, carbohydrates, and fats.

18. The device of claim 1 wherein the chemical or biological component, with which the primary reactive molecules on the first distal ends are capable of reacting to decrease the hydrophobicity of the first distal ends, includes a member selected from a group consisting of herbicides, pesticides, and heavy metals.

19. The device of claim 1, wherein the primary reactive molecules include a member selected from a group consisting of antibodies and single stranded polynucleotides.

20. The device of claim 1, wherein the first distal ends of each of the plurality of first raised elements has a hydrophobic coating.

* * * * *